United States Patent [19]

Naglieri et al.

[11] 4,002,678
[45] Jan. 11, 1977

[54] PREPARATION OF CARBOXYLIC ACID ANHYDRIDES

[75] Inventors: Anthony N. Naglieri, Pine Brook; Nabil Rizkalla, River Vale, both of N.J.

[73] Assignee: Halcon International, Inc., New York, N.Y.

[22] Filed: Dec. 22, 1975

[21] Appl. No.: 643,208

[52] U.S. Cl. ................................ 260/549; 260/546
[51] Int. Cl.$^2$ .................. C07C 51/54; C07C 51/56
[58] Field of Search ........................... 260/546, 549

[56] References Cited

UNITED STATES PATENTS

| | | | |
|---|---|---|---|
| 2,497,304 | 2/1950 | Gresham et al. | 260/546 |
| 2,593,440 | 4/1952 | Hagemeyer | 260/546 |
| 2,607,787 | 8/1952 | Mason | 260/546 |
| 2,730,546 | 1/1956 | Reppe et al. | 260/549 |
| 2,739,169 | 3/1956 | Hugemeyer | 260/546 |
| 2,789,137 | 4/1957 | Reppe et al. | 260/549 |
| 3,641,071 | 2/1972 | Fenton | 260/546 |
| 3,641,074 | 2/1972 | Fenton | 260/546 |
| 3,852,346 | 12/1974 | Forster et al. | 260/546 |
| 3,887,595 | 6/1975 | Mozaki | 260/546 |
| 3,927,078 | 12/1975 | Lapporte et al. | 260/549 |

*Primary Examiner*—Norman Morgenstern
*Attorney, Agent, or Firm*—William C. Long; David Dick; Riggs T. Stewart

[57] ABSTRACT

A carboxylic acid anhydride, such as acetic anhydride, is prepared from a carboxylate ester or a hydrocarbyl ether in carbonylation processes comprising the use of an iodide, carbon monoxide and a nickel-chromium catalyst in the presence of a promoter comprising an organo-nitrogen compound or an organo-phosphorus compound wherein the nitrogen and phosphorus are trivalent.

6 Claims, No Drawings

PREPARATION OF CARBOXYLIC ACID ANHYDRIDES

This invention relates to the preparation of anhydrides of carboxylic acids, more particularly mono-carboxylic acids, and especially the anhydrides of lower alkanoic acids, such as acetic anhydride, by carbonylation.

Acetic anhydride has been known as an industrial chemical for many years and large amounts are used in the manufacture of cellulose acetate. It has commonly been produced on an industrial scale by the reaction of ketene and acetic acid. It is also known that acetic anhydride can be produced by the decomposition of ethylidene diacetate, as well as by the oxidation of acetaldehyde, for example. Each of these "classic" processes has well-known drawbacks and disadvantages and the search for an improved process for the production of acetic anhydride has been a continuing one. Proposals for producing anhydrides by the action of carbon monoxide upon various reactants (carbonylation) have been described, for example, in Reppe et al U.S. Pat. Nos. 2,729,561 2,730,546, and 2,789,137. However, such prior proposals involving carbonylation reactions have required the use of very high pressures. More recently, carbonylation at lower pressures has been proposed but only as a route to the preparation of acetic acid. French Pat. No. 1,573,130, for example, describes the carbonylation of methanol and mixtures of methanol with methyl acetate in the presence of compounds of Group VIII noble metals such as iridium, platinum, palladium, osmium and ruthenium and in the presence of bromine or iodine under more moderate pressures than those contemplated by Reppe et al. Similarly, South African Pat. No. 68/2174 produces acetic acid from the same reactants using a rhodium component with bromine or iodine. Schultz (U.S. Pat. Nos. 3,689,533 and 3,717,670) has disclosed a vapor-phase process for acetic acid production employing various catalysts comprising a rhodium component dispersed on a carrier. None of these later carbonylation disclosures, however, refers to or contemplates the preparation of acetic anhydride or other carboxylic acid anhydrides.

Most recently, improved processes for preparing carboxylic acid anhydrides, including acetic anhydride, have been disclosed in co-pending applications of Colin Hewlett Ser. No. 394,220, filed Sept. 4, 1973, Ser. No. 467,977, filed May 8, 1974, and Ser. No. 554,933, filed Mar. 3, 1975 and in the co-pending application of Nabil Rizkalla, Ser. No. 556,750, filed Mar. 10, 1975. In all of these recent processes, however, a Group VIII noble metal is an essential catalyst component. Consequently, while entirely effective, these processes suffer from the need to employ expensive, relatively rare metals.

It is an object of the present invention to provide an improved process for the manufacture of carboxylic acid anhydrides, especially lower alkanoic anhydrides, such as acetic anhydride, which requires neither high pressures nor Group VIII noble metals.

In accordance with the invention, it has been surprisingly discovered that a carboxylic ester and/or a hydrocarbyl ether can be carbonylated at relatively low pressures if the carbonylation is carried out in the presence of a multiple or co-catalyst comprising a nickel component and a chromium component in the presence of an iodide, and in the presence of a promoter comprising an organo-nitrogen compound or an organo-phosphorus compound wherein the nitrogen and phosphorus are trivalent. It has been discovered that this nickel-chromium co-catalyst-promoter system makes possible carbonylation at relatively low pressures, especially carbon monoxide partial pressures, in contrast to the process disclosed in Reppe et al U.S. Pat. No. 2,729,651 in which, while employing a nickel-containing catalyst, the patentees find it necessary to use pressures of at least 200 atmospheres in their examples.

Thus, in accordance with the invention, carbon monoxide is reacted with a carboxylate ester, especially a lower alkyl alkanoate, or a hydrocarbyl ether such as a lower alkyl ether, to produce a carboxylic anhydride, such as a lower alkanoic anhydride, the carbonylation taking place in the presence of an iodide e.g., a hydrocarbyl iodide, especially a lower alkyl iodide, such as methyl iodide. Thus, acetic anhydride, for example, can be effectively prepared in a representative case by subjecting methyl acetate or dimethyl ether to carbonylation in the presence of methyl iodide. In all cases, the carbonylation is carried out under anhydrous conditions in the presence of the co-catalyst promoter-system described above. Moreover, an ester-ether mixture can be carbonylated if desired.

It will be understood that the iodine moiety does not have to be added to the system as a hydrocarbyl iodide but may be supplied as another organic iodide or as the hydroiodide or other inorganic iodide, e.g., a salt, such as the alkali metal or other metal salt, or even as elemental iodine. Following the reaction the organic components of the reaction mixture are readily separated from one another, as by fractional distillation.

In like manner, other lower alkanoic anhydrides, i.e., anhydrides of lower alkanoic acids, such as propionic anhydride, butyric anhydrides, and valeric anhydrides, can be produced by carbonylating the corresponding lower alkyl alkanoate or a lower alkyl ether. Similarly, other carboxylic acid anhydrides, e.g., the anhydrides of other alkanoic acids, such as those containing up to 12 carbon atoms, for example capric anhydrides, caprylic anhydrides, and lauric anhydrides, and like higher anhydrides are produced by carbonylating the corresponding ester, e.g., alkyl alkanoates containing up to 11 carbon atoms in the alkyl group and up to 12 carbon atoms in the carboxylate group, or aryl esters, or the corresponding ether, such as heptyl caprylate, nonyl decanoate, undecyl laurate, phenyl benzoate, heptyl ether, nonyl ether, phenyl ether, and the like.

It is preferred that the reactants be selected to that the resulting anhydride will be a symmetrical anhydride, i.e., having two identical acyl groups, viz., wherein R in equations (1) and (2) is the same in each instance, but it is within the scope of the invention to produce non-symmetrical or mixed anhydrides and this can be readily effected by using different combinations of reactants, e.g., by using compounds having different R groups in the foregoing reactions, as will be obvious to persons skilled in the art.

The above-described reactions can be expressed as follows:

$$CO + RCOOR \rightarrow (RCO)_2O \qquad (1)$$

$$2CO + ROR \rightarrow (RCO)_2O \qquad (2)$$

wherein R is a hydrocarbyl radical which may be saturated, e.g., alkyl of 1 to 11 carbon atoms, or monocyclic aryl, e.g., phenyl or aralkyl, e.g., benzyl. Preferably, R is lower alkyl, i.e., an alkyl group of 1 to 4 carbon atoms, such as methyl, ethyl, n-propyl, i-propyl, n-butyl, sec-butyl, and t-butyl.

The hydrocarbyl radical may be substituted with substituents which are inert in the reactions of the invention.

The more volatile components such as alkyl iodide and unreacted ether or ester in the final product mixture can be readily removed, as by distillation, for recycling, and the net yield of product is substantially exclusively the desired carboxylic anhydride. In the case of liquid-phase reaction which is preferred, the organic compounds are easily separated from the metal-containing components, as by distillation. The reaction is suitably carried out in a reaction zone to which the carbon monoxide, the ester or ether, the iodide and the nickel-chromium catalyst and the promoters are fed. No water is produced in the above-described reactions and anhydrous or substantially anhydrous conditions are employed.

In carrying out the process of the invention, a wide range of temperatures, e.g., 25° to 350° C are suitable but temperatures of 100° to 250° C are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but, as previously mentioned, it is a feature of the invention that excessively high pressures, which require special high-pressure equipment, are not necessary. In general, the reaction is effectively carried out by employing a carbon monoxide partial pressure which is preferably 15 to 1000 psi and most preferably 30 to 200 psi, although carbon monoxide partial pressures of 1 to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and in this case the reaction can be advantageously carried out in an autoclave or similar apparatus. The final reaction mixture will normally contain volatile components such as a hydrocarbyl iodide, unreacted ester or ether along with the product anhydride and these volatile components, after separation from the anhydride, can be recycled to the reaction. At the end of the desired residence time the reaction mixture is separated into its several constituents, as by distillation. Preferably, the reaction product is introduced into a distillation zone which may be a fractional distillation column, or a series of columns, effective to separate the volatile components from the product anhydride and to separate the product anhydride from the less volatile catalyst and promoter components of the reaction mixture. The boiling points of the volatile components are sufficiently far apart that their separation by conventional distillation presents no particular problem. Likewise, the higher boiling organic components can be readily distilled away from the metal cocatalyst components and any organic promoter which may be in the form of a relatively non-volatile complex. Nickel-chromium catalyst, as well as promoter can then be combined with fresh amounts of ester or ether and carbon monoxide and reacted to produce additional quantities of anhydride.

The ratio of ester or ether to the halide in the reaction system can vary over a wide range. Typically, there are used 0.1 to 1000 moles of the ester or ether per mole of halide, preferably 1 to 30 moles per mole.

The process is advantageously carried out in the presence of a solvent or diluent, particularly when the reactant has a relatively low boiling point, as in the case of dimethyl ether. The presence of a higher boiling solvent or diluent, which may be the product anhydride itself, e.g., acetic anhydride in the case of dimethyl ether, or which may be the corresponding ester, e.g., methyl acetate, again in the case of methyl ether, will make it possible to employ more moderate total pressure. Alternatively, the solvent or diluent may be any organic solvent which is inert in the environment of the process such as hydrocarbons, e.g., octane, benzene, toluene, or carboxylic acids, e.g., acetic acid, and the like. The carboxylic acid, when used, should preferably correspond to the anhydride being produced. A solvent or diluent is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen methane, and noble gases can be present if desired. The presence of inert diluents does not affect the carbonylation reaction but their presence makes it necessary to increase the total pressure in order to maintain the desired CO partial pressure. The carbon monoxide, like other reactants should, however, be essentially dry, i.e., the CO and the other reactants should be reasonably free from water. The presence of minor amounts of water such as may be found in the commercial forms of the reactants is, however, entirely acceptable. It is preferable that the amount of moisture be kept to a minimum, since the presence of water has been found to have an adverse effect upon the activity of the cocatalyst promoter system. Hydrogen which may be present as an impurity is not objectionable and even may tend to stabilize the catalyst. Indeed, in order to obtain low CO partial pressures the CO fed may be diluted with hydrogen or any inert gas such as those above mentioned.

The nickel and chromium catalyst components can be employed in any convenient form, viz., in the zero valent state or in any higher valent form. For example, the nickel and chromium to be added may be the metals themselves in finely divided form, or a compound, both organic or inorganic, which is effective to introduce the nickel and chromium into the reaction system. Thus, typical compounds include the carbonate, oxide, hydroxide, bromide, iodide, chloride, oxyhalide, hydride, lower alkoxide (methoxide) phenoxide or chromium and nickel carboxylates wherein the carboxylate ion is derived from an alkanoic acid of 1 to 20 carbon atoms such as acetates, butyrates, decanoates, laurates, benzoates, and the like. Similarly, complexes of nickel or chromium can be employed, for example, nickel, or chromium carbonyls and metal alkyls as well as chelates, association compounds and enol salts. Examples of other complexes include bis-(triphenyl phosphine) nickel dicarbonyl, tricyclopentadienyl trinickel dicarbonyl, tetrakis (triphenyl phosphite) nickel, benzene chromium tricarbonyl, cycloheptatriene chromium tricarbonyl and dicyclopentadienyl chromium.

Included among the catalyst components listed above are complexes of nickel and/or chromium with organic promoter ligands derived from the organic promoters hereinafter described. Particularly preferred are the elemental forms, compounds which are iodides, and organic salts, e.g., salts of the monocarboxylic acid corresponding to the anhydride being produced. It will be understood that the foregoing compounds and complexes are merely illustrative of suitable forms of the nickel-chromium co-catalyst and are not intended to be limiting.

The nickel and chromium catalyst components employed may contain impurities normally associated with the commercially available metal or metal compounds and need not be purified any further.

The organic promoter is an organo-nitrogen or organo-phosphorus compound wherein the nitrogen and phosphorus are trivalent. Preferably, however, the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexylmethylamine, 2,6-diaminopyridine, 2-quinolinol, and N,N-diethyltoluamide.

The organo-phosphorus promoter is preferably a phosphine, e.g., a phosphine of the formula

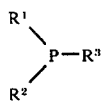

wherein $R^1$, $R^2$ and $R^3$ may be the same or different, and are alkyl, cycloalkyl, aryl groups, amide groups or halogen atoms, preferably containing up to 1 to 20 carbon atoms in the case of alkyl and cycloalkyl groups and 6 to 18 carbon atoms in the case of aryl groups. Typical phosphines include trimethylphosphine, tripropylphosphine, tricycohexylphosphine and triphenylphosphine.

Although generally the organic promoters are added separately to the catalyst system, it is also possible to add them as complexes with the nickel and/or chromium such as bis(triphenyl phosphine) nickel dicarbonyl, tricyclopentadienyl trinickel, dicarbonyl, and tetrakis (triphenyl phosphite) nickel. Both free organic promoters and complexed promoters can also be used. Indeed, when a complex of the organic promoter and nickel and/or chromium is used, free organic promoter can also be added as well.

The amount of nickel and chromium is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each component of the co-catalyst is employed in the amount of 1 mol per 10 to 100,000 mols of ester or ether, preferably 1 mol per 100 to 10,000 mols of ester or ether, and most preferably 1 mol per 500 to 2000 mols of ester or ether.

The ratio of nickel to chromium can vary. Typically, it is one mol of the nickel component per 0.1 to 20 mols of chromium component, preferably the nickel component is used in the amount of 1 mol per 0.5 to 5 mols, most preferably 1 mol per 2 mols of chromium component.

The quantity of organic promoter can also vary widely but typically it is used in the amount of 1 mol per 1 to 10,000 mols of ester or ether, preferably 1 mol per 10 to 1000, most preferably 1 mol per 15 to 200 mols of ester or ether.

As previously mentioned, in the working up of the reaction mixtures, e.g., by distillation, the promoter components can be readily recovered and recycled to the reaction. The chromium and nickel generally remain as the least volatile components, and are recycled or otherwise handled together. They may, however, distill with the volatile components, e.g., in the case of nickel carbonyl. The same is true of the promoter components.

When an ether is used as the reactant, the corresponding ester is formed as an intermediate, e.g., methyl acetate is formed when dimethyl ether is carbonylated in accordance with the invention. This intermediate ester may be recovered from the reaction mixture, if desired, e.g., by fractional distillation, for example during the separation of the volatile components of the reaction mixture as described above.

It will be apparent that the above-described reactions lend themselves readily to continuous operation in which the reactants and catalyst, preferably in combination with the promoter, are continuously supplied to the appropriate reaction zone and the reaction mixture continuously distilled to separate the volatile organic constituents and to provide the desired product or products, e.g., carboxylic acid anhydride, with the other organic components being recycled and, in the case of liquid-phase reaction, a residual nickel-chromium-containing (and promoter-containing) fraction also being recycled. It has been observed that hydrogen, e.g., used as a CO diluent as indicated above, is of value in maintaining the catalyst at maximum activity on repeated recycle. During continuous operation, it will be apparent that the iodine moiety remains in the system at all times subject only to occasional handling losses or purges. The small amount of iodine makeup which may be needed from time to time is preferably effected by supplying the iodine in the form of the hydrocarbyl iodide but, as pointed out above, the iodine moiety may also be supplied as another organic iodide or as the hydrogen iodide or other inorganic iodide, e.g., a salt, such as the alkali metal or other metal salts, or as elemental iodine.

The following examples will serve to provide a fuller understanding of the invention, but it is to be understood that they are given for illustrative purposes only, and are not to be construed as limitative of the invention. In the examples, all parts are on a molar basis and all percentages are by weight, unless otherwise indicated. The various reactants and catalyst components are charged to the reaction vessel which is then closed and brought to the reaction temperature indicated.

EXAMPLE 1

Methyl acetate (100 parts), methyl iodide (18 parts), nickel acetate (0.8 part), chromium carbonyl (2 parts) and 2-hydroxy pyridine (1.6 parts) are charged to a glass-lined bomb which is pressured to 400 psig with carbon monoxide at room temperature and sealed. The bomb is then heated and stirred for 17 hours at 150° C. At this temperature the initial total pressure is approximately 750 psig and the initial partial pressure of carbon monoxide is approximately 550 psi. Analysis of the reaction mixture by gas chromatography (G. C.) at the end of the 17-hour reaction period shows it to contain 38 wt. % of acetic anhydride, representing a conversion of 54%.

EXAMPLE 2

Using the procedure of Example 1, methyl acetate (100 parts), methyl iodide (18 parts), nickel acetate (0.8 part), chromium carbonyl (2 parts) and 2-quinolinol (1.6 parts) are reacted in a glass-lined bomb which is pressured to 400 psig with carbon monoxide at room temperature and then heated and stirred for 17 hours at 150° C. As in Example 1, at this temperature the initial total pressure is approximately 750 psig and the initial partial pressure of carbon monoxide is approximately 550 psi. G. C. analysis of the reaction mixture shows it to contain 19 wt. % acetic anhydride, representing a conversion of 21%.

EXAMPLE 3

Again using the procedure of Example 1, methyl acetate (100 parts), methyl iodide (18 parts), nickel acetate (0.8 part), chromium carbonyl (2 parts) and 1-methyl pyrrolidinone (1.6 parts) are charged to a glass-lined bomb which is pressured to 400 psig with carbon monoxide at room temperature and sealed. The bomb is then heated and stirred for 17 hours at 150° C. At this temperature the initial total pressure is approximately 750 psig and the initial partial pressure of carbon monoxide is approximately 550 psi. G. C. analysis of the reaction mixture shows it to contain 9.8 wt. % acetic anhydride, representing a conversion of 10.6%.

EXAMPLE 4

Example 1 is repeated except that the charge includes 1.6 parts of 2-imidazolidone instead of 2-hydroxypyridine. G. C. analysis of the reaction mixture after the 17-hour reaction period shows it to contain 14.7 wt. % of acetic anhydride, representing a conversion of 16%.

EXAMPLE 5

Example 1 is again repeated except that 1.6 parts of N,N-dimethyl acetamide are substituted for the 2-hydroxy pyridine. As in the case of the preceding examples at the 150° C reaction temperature the initial total pressure is approximately 750 psig and the initial partial pressure of carbon monoxide is approximately 550 psi. G. C. analysis of the reaction mixture shows it to contain 8.4 wt. % acetic anhydride, representing a conversion of 9%.

EXAMPLE 6

Methyl acetate (100 parts), methyl iodine (18 parts), nickel acetate (0.8 part), chromium carbonyl (2 parts) and N, N-dicyclohexyl methyl amine (1.6 parts) are charged to a glass-lined bomb which, as in the preceding examples, is pressured to 400 psig with carbon monoxide at room temperature and sealed and then heated and stirred for 17 hours at 150° C. At this temperature the initial total pressure is approximately 750 psig and the initial partial pressure of carbon monoxide is approximately 550 psi. G. C. analysis of the reaction mixture shows it to contain 13.6 wt. % acetic anhydride, representing a conversion of 15%.

EXAMPLE 7

Example 6 is repeated but 1.6 parts of 2,6-diamino pyridine are substituted for the N,N-dicyclohexyl methyl amine. At the 150° C reaction temperature the initial total pressure is approximately 750 psig and the initial partial pressure of carbon monoxide is approximately 550 psi. G. C. analysis of the reaction mixture shows it to contain 10 wt. % acetic anhydride, representing a conversion of 11%.

EXAMPLE 8

Example 6 is again repeated but 1.6 parts of N,N-diethyl-m-toluamide are substituted for the N,N-dicyclohexyl methyl amine. At the 150° C reaction temperature the initial total pressure is approximately 750 psig and the initial partial pressure of carbon monoxide is approximately 550 psi. G. C. analysis of the reaction mixture shows it to contain 42 wt. % acetic anhydride, representing a conversion of 51%.

EXAMPLE 9

Methyl acetate (100 parts), methyl iodide (18 parts), nickel acetate (0.8 part), chromium hexacarbonyl (2 parts) and triphenyl phosphine (1.6 parts) are charged to a glass-lined bomb which, as in the preceding examples, is then pressured to 400 psig with carbon monoxide at room temperature and sealed and then heated and stirred for 17 hours at 150° C. At this temperature the initial total pressure is approximately 750 psig and the initial partial pressure of carbon monoxide is approximately 550 psi. G. C. analysis of the reaction mixture shows it to contain 45 wt. % acetic anhydride, representing a conversion of 55%.

EXAMPLE 10

Methyl acetate (100 parts), methyl iodide (17 parts), bis-(triphenyl phosphine) nickel dicarbonyl (0.8 part) and chromium hexacarbonyl (2 parts) are charged into a stirred Hastelloy-C pressure vessel which is pressured to 275 psig with carbon monoxide and the vessel is then heated at 153° C for 7 hours. At the reaction temperature the carbon monoxide has an initial partial pressure of 370 psi, and during the reaction period carbon monoxide is continuously supplied to maintain a continuous total pressure in the vessel of 550 psig. After the 7-hour reaction time, G. C. analysis of the reaction mixture shows it to contain 48 wt. % acetic anhydride, representing a conversion of 64%.

EXAMPLE 11

Methyl acetate (100 parts), methyl iodide (17 parts), bis-(triphenyl phosphine) nickel dicarbonyl (0.8 part) and chromium hexacarbonyl (2 parts) are charged into a stirred Hastelloy-C pressure vessel which is pressured to 600 psig with carbon monoxide and the vessel is then heated at 153° C for 5½ hours. At the reaction temperature the carbon monoxide has an initial partial pressure of 850 psi and during the reaction period, carbon monoxide is continuously supplied to maintain a continuous total pressure in the vessel of 750 psig. After the 5½-hour reaction time, G. C. analysis of the reaction mixture shows it to contain 56 wt. % acetic anhydride, representing a conversion of 70%.

EXAMPLE 12

Methyl acetate (100 parts), methyl iodide (17 parts), nickel tetracarbonyl (0.8 part), triphenyl phosphine (1.7 parts) and chromium hexacarbonyl (2 parts) are charged into a stirred Hastelloy-C pressure vessel which is pressured to 370 psig with carbon monoxide and hydrogen (9:1 ratio) and the vessel is then heated at 153° C for 5½ hours. At the reaction temperature the carbon monoxide has an initial partial pressure of 480 psi, and during the reaction period, carbon monoxide is continuously supplied to maintain a continuous total pressure in the vessel of 725 psig. After the 5½-hour reaction time, G. C. analysis of the reaction mixture shows it to contain 58 wt. % acetic anhydride, representing a conversion of 73%.

EXAMPLE 13

Methyl acetate (100 parts), methyl iodide (17 parts), bis-(triphenyl phosphine) nickel dicarbonyl (0.8 part), triphenyl phosphine (1.2 parts) and chromium hexacarbonyl (2 parts) are charged into a stirred Hastelloy-C pressure vessel which is pressured to 390 psig with carbon monoxide and hydrogen (9:1 ratio) and the vessel is then heated at 153° C for 6½ hours. At the reaction temperature the carbon monoxide has an initial partial pressure of 500 psi, and during the reaction period, carbon monoxide is continuously supplied to maintain a continuous total pressure in the vessel of 750 psig. After the 6½-hour reaction time, G. C. analysis of the reaction mixture shows it to contain 59.4 wt. % acetic anhydride, representing a conversion of 77%.

EXAMPLE 14

Methyl acetate (100 parts), methyl iodide (17 parts), bis-(triphenyl phosphine) nickel dicarbonyl (0.8 part) and triphenyl phosphine (2.4 parts) are charged into a stirred Hastelloy-C pressure vessel which is pressured to 400 psig with carbon monoxide and hydrogen (9:1 ratio) and the vessel is then heated at 154° C for 6½ hours. At the reaction temperature the carbon monoxide has an initial partial pressure of 525 psi, and during the reaction period, carbon monoxide is continuously supplied to maintain a continuous total pressure in the vessel of 775 psig. After the 6½-hour reaction time, G. C. analysis of the reaction mixture shows it to contain 7.3 wt. % acetic anhydride, representing a conversion of 8%. Comparison of this example with Example 13 shows the significance of the presence of the chromium component.

EXAMPLE 15

Methyl acetate (100 parts), iodine (10 parts), nickel acetate (1 part), chromium carbonyl (2 parts) and triphenyl phosphine (3 parts) were heated at 150° C for 17 hours under an atmosphere of carbon monoxide (400 psig at room temperature). At this temperature the initial total pressure is approximately 750 psig and the initial carbon monoxide partial pressure is approximately 550 psi. After the 17-hour reaction time, G. C. analysis of the reaction mixture shows it to contain 33 wt. % acetic anhydride, representing a conversion of 33%.

EXAMPLE 16

Methyl acetate (100 parts), methyl iodide (10 parts), nickel acetate (1 part), chromic iodide (2 parts) and triphenyl phosphine (3 parts) were heated at 150° C for 17 hours under an atmosphere of carbon monoxide (400 psig at room temperature). At this temperature the initial total pressure is approximately 750 psig and the initial carbon monoxide partial pressure is approximately 550 psi. After the 17-hour reaction time, G. C. analysis of the reaction mixture shows it to contain 43 wt. % acetic anhydride, representing a conversion of 49%.

EXAMPLE 17

Methyl acetate (100 parts), methyl iodide (5 parts), nickel iodide (4 parts), chromium hexacarbonyl (2 parts) and triphenyl phosphine (3 parts) were heated at 150° C for 17 hours under an atmosphere of carbon monoxide (400 psig at room temperature). At this temperature the initial total pressure is approximately 750 psig and the initial carbon monoxide partial pressure is approximately 550 psi. After the 17-hour reaction time, G. C. analysis of the reaction mixture shows it to contain 39 wt. % acetic anhydride, representing a conversion of 45%.

EXAMPLE 18

Methyl acetate (40 parts), dimethyl ether (60 parts), bis-(triphenyl phosphine) nickel dicarbonyl (0.8 part), triphenyl phosphine (0.5 part), methyl iodide (18 parts) and chromium hexacarbonyl (2 parts) are charged to a glass-lined bomb which is pressured to 500 psig carbon monoxide at room temperature. The vessel is closed and then stirred for 14 hours at 145° C. At this temperature the initial total pressure is approximately 1450 psig and the initial partial pressure of carbon monoxide is approximately 700 psi. G. C. analysis of the reaction mixture at the end of the 14-hour reaction period shows it to contain 50 parts dimethyl ether, 45 parts methyl acetate and 5 parts acetic anhydride.

EXAMPLE 19

Dimethyl ether (100 parts) N, N-diethyl-m-toluamide (18 parts), bis-(triphenyl phosphine) nickel dicarbonyl (1.3 parts), methyl iodide (14 parts), and chromium hexacarbonyl (2 parts) are charged to a stainless-steel bomb which is pressured to 500 psig at room temperature with carbon monoxide. The vessel is then closed, heated and stirred for 14 hours at 150° C. At the reaction temperature the total pressure is less than 1700 psig and the initial CO partial pressure is less than 800 psi. G. C. analysis of the reaction mixture at the end of the 14-hour reaction period shows it to contain 13 parts dimethyl ether, 24 parts methyl acetate and 63 parts acetic anhydride.

EXAMPLE 20

Dimethyl ether (100 parts), N,N-diethyl-m-toluamide (18 parts), bis-triphenyl phosphine) nickel carbonyl (1.3 parts), methyl iodide (26 parts) and chromium hexacarbonyl (1.5 parts) are charged to a stainless-steel bomb which is pressured at room temperature to 600 psig with carbon monoxide and hydrogen (5:1 ratio). The vessel is then closed, heated and stirred for 16 hours at 150° C. At the reaction temperature the total pressure is less than 800 psi. G. C. analysis of the reaction mixture at the end of the 16-hour reaction period shows it to contain 7 parts dimethyl ether, 54 parts methyl acetate and 38 parts acetic anhydride.

EXAMPLE 21

Dimethyl ether (75 parts), methyl acetate (25 parts), nickel acetate (0.9 part), triphenyl phosphine (1.2 parts), methyl iodide (10 parts) and chromium hexacarbonyl (1.4 parts) are charged to a stainless-steel bomb which is pressured at room temperature to 600 psig with carbon monoxide and hydrogen (9:1 ratio). The vessel is then closed, heated and stirred for 14 hours at 150° C. At the reaction temperature the total pressure is 1800 psig and the initial CO partial pressure is 750 psi. G. C. analysis of the reaction mixture at the end of the 14-hour reaction period shows it to contain 38 parts dimethyl ether, 52 parts methyl acetate and 10 parts acetic anhydride.

EXAMPLE 22

Dimethyl ether (100 parts), ethylene glycol diacetate (30 parts), nickel acetate (1.2 parts), triphenyl phosphine (4 parts), methyl iodide (17 parts) and chromium hexacarbonyl (2.4 parts) are charged to a stainless-steel bomb which is pressured at room temperature to 600 psig with carbon monoxide and hydrogen (9:1 ratio). The vessel is then closed, heated and stirred for 14 hours at 150° C. At the reaction temperature the total pressure is 1680 psig and the initial CO partial pressure is 750 psi. G. C. analysis of the reaction mixture at the end of the 14-hour reaction period shows it to contain 28 parts dimethyl ether, 44 parts methyl acetate and 28 parts acetic anhydride.

EXAMPLE 23

Dimethyl ether (72 parts), acetic anhydride (28 parts), bis-(triphenyl phosphine) nickel carbonyl (0.65 part), triphenyl phosphine (1.6 parts), methyl iodide (13 parts) and chromium hexacarbonyl (1.9 parts) are charged to a stainless-steel bomb which is pressured at room temperature to 600 psig with carbon monoxide and hydrogen (9:1 ratio). The vessel is closed, heated and stirred for 13 hours at 150° C. At the reaction temperature the total pressure is 1750 psig and the initial CO partial pressure is 750 psi. G. C. analysis of the reaction mixture at the end of the 13-hour reaction period shows it to contain 25 parts dimethyl ether, 40 parts methyl acetate and 35 parts acetic anhydride.

EXAMPLE 24

Dimethyl ether (100 parts), toluene (54 parts), nickel acetate (1.1 parts), triphenyl phosphine (4 parts), methyl iodide (17 parts) and chromium hexacarbonyl (2.4 parts) are charged to a stainless-steel bomb which is pressured to 600 psig at room temperature with carbon monoxide and hydrogen (9:1 ratio). The vessel is closed, heated and stirred for 15 hours at 150° C. At the reaction temperature the total pressure is 1630 psig and the initial CO partial pressure is 750 psi. G. C. analysis of the reaction mixture at the end of the 15-hour reaction period shows it to contain 49 parts dimethyl ether, 49 parts methyl acetate and 2 parts acetic anhydride.

EXAMPLE 25

Methyl acetate (100 parts), methyl iodide (17 parts), bis-(triphenyl phosphine) nickel dicarbonyl (0.8 part) and chromium hexacarbonyl (2 parts) are charged into a stirred Hastelloy-C pressure vessel which is pressured to 120 psig at room temperature with carbon monoxide and hydrogen (1:1 ratio) and the vessel is then closed and heated with stirring at 153° C for 5 hours. At the reaction temperature the carbon monoxide has an initial partial pressure of 85 psi and during the reaction period, carbon monoxide is continuously supplied to maintain a continuous total pressure in the vessel of 350 psig. After the 5-hour reaction time, G. C. analysis of the reaction mixture shows it to contain 38 wt. % acetic anhydride, representing a conversion of 45%.

EXAMPLE 26

Methyl acetate (100 parts), methyl iodide (17 parts) and nickel diiodide (2 parts) are charged to a glass-lined bomb which is pressured to 550 psig with carbon monoxide at room temperature and sealed. The bomb is then heated and stirred for 17 hours at 150° C. At this temperature the initial total pressure is approximately 970 psig and the initial partial pressure of carbon monoxide is approximately 775 psi. G. C. analysis of the reaction mixture at the end of the 17-hour reaction period shows it to contain no acetic anhydride.

What is claimed is:
1. A process for the preparation of an anhydride of a mono-carboxylic acid which comprises reacting carbon monoxide and an alkyl or aryl carboxylic acid ester or an alkyl or aryl ether under substantially anhydrous conditions at elevated temperature and atmospheric pressure in the presence of a halide which is an iodide or a bromide and a catalyst comprising nickel and chromium in the presence of a promoter comprising an organo-trivalent nitrogen compound or a phosphine.
2. A process as defined in claim 1, wherein the anhydride is a lower alkanoic anhydride, the carboxylic acid ester is a lower alkyl lower alkanoate and the ether is a lower alkyl ether.
3. A process as defined in claim 1, wherein the promoter is an organo-trivalent nitrogen compound.
4. A process as defined in claim 1, wherein the promoter is a phosphine.
5. A process as defined in claim 1, wherein the anhydride is acetic anhydride, the carboxylic acid ester is methyl acetate and the ether is dimethyl ether.
6. A process as defined in claim 1, wherein the reaction is carried out under a carbon monoxide partial pressure up to 1000 psi.

* * * * *

UNITED STATES PATENT AND TRADEMARK OFFICE
CERTIFICATE OF CORRECTION

PATENT NO. : 4,002,678
DATED : January 11, 1977
INVENTOR(S) : Anthony N. Naglieri and Nabil Rizkalla It is certified that error appears in the above-identified patent and that said Letters Patent are hereby corrected as shown below:

Col. 12, line 40, before "atmospheric", insert -- super- --.

Signed and Sealed this

Twenty-eighth Day of February 1978

[SEAL]

Attest:

RUTH C. MASON
Attesting Officer

LUTRELLE F. PARKER
Acting Commissioner of Patents and Trademarks